United States Patent [19]
Gray

[11] Patent Number: 5,108,449
[45] Date of Patent: Apr. 28, 1992

[54] FEMORAL COMPONENT FOR A HIP PROSTHESIS

[76] Inventor: Frank B. Gray, 5104 Lyons View Dr., Knoxville, Tenn. 37979

[21] Appl. No.: 637,545

[22] Filed: Dec. 31, 1990

[51] Int. Cl.$^5$ .............................................. A61F 2/32
[52] U.S. Cl. ............................ 623/23; 606/60; 606/69
[58] Field of Search ............... 623/16, 18, 19, 20, 623/22, 23; 606/60, 62, 64, 67, 69, 70, 72

[56] References Cited

U.S. PATENT DOCUMENTS

| | | |
|---|---|---|
| 3,906,550 | 9/1975 | Rostoker et al. |
| 4,365,358 | 12/1982 | Judet et al. |
| 4,514,865 | 5/1985 | Harris |
| 4,676,797 | 6/1987 | Anapliotis et al. |
| 4,714,471 | 12/1987 | Hans Grundei |
| 4,851,007 | 7/1989 | Gray |

FOREIGN PATENT DOCUMENTS

| | | | |
|---|---|---|---|
| 0000549 | 7/1978 | European Pat. Off. | |
| 0201407 | 11/1986 | European Pat. Off. | 623/23 |
| 3607824 | 9/1987 | Fed. Rep. of Germany | 623/23 |
| 2166359 | 5/1984 | United Kingdom | 623/23 |
| 8603962 | 7/1986 | World Int. Prop. O. | 623/23 |

*Primary Examiner*—David J. Isabella
*Attorney, Agent, or Firm*—Pitts and Brittian

[57] ABSTRACT

A femoral component (10) for a hip prosthesis. The femoral component (10) includes a proximal body (18) having a lower portion for implantation into the proximal femur, and a neck portion (26) carried by the upper portion of the proximal body (18). A head portion (30) is mounted on the neck portion (26) for being rotatably received in the acetabulum (14) of an operatively associated acetabular component (12). Further, an extramedullary buttressing plate (38) is provided for supporting the proximal body (18) in a desired implanted position. The buttressing plate (38) includes an elongated body (40) for being secured to the exterior of the femur along a selected portion of the length of the femoral shaft, the elongated (40) body having a proximal end portion (44) for engaging the proximal body (18).

18 Claims, 3 Drawing Sheets

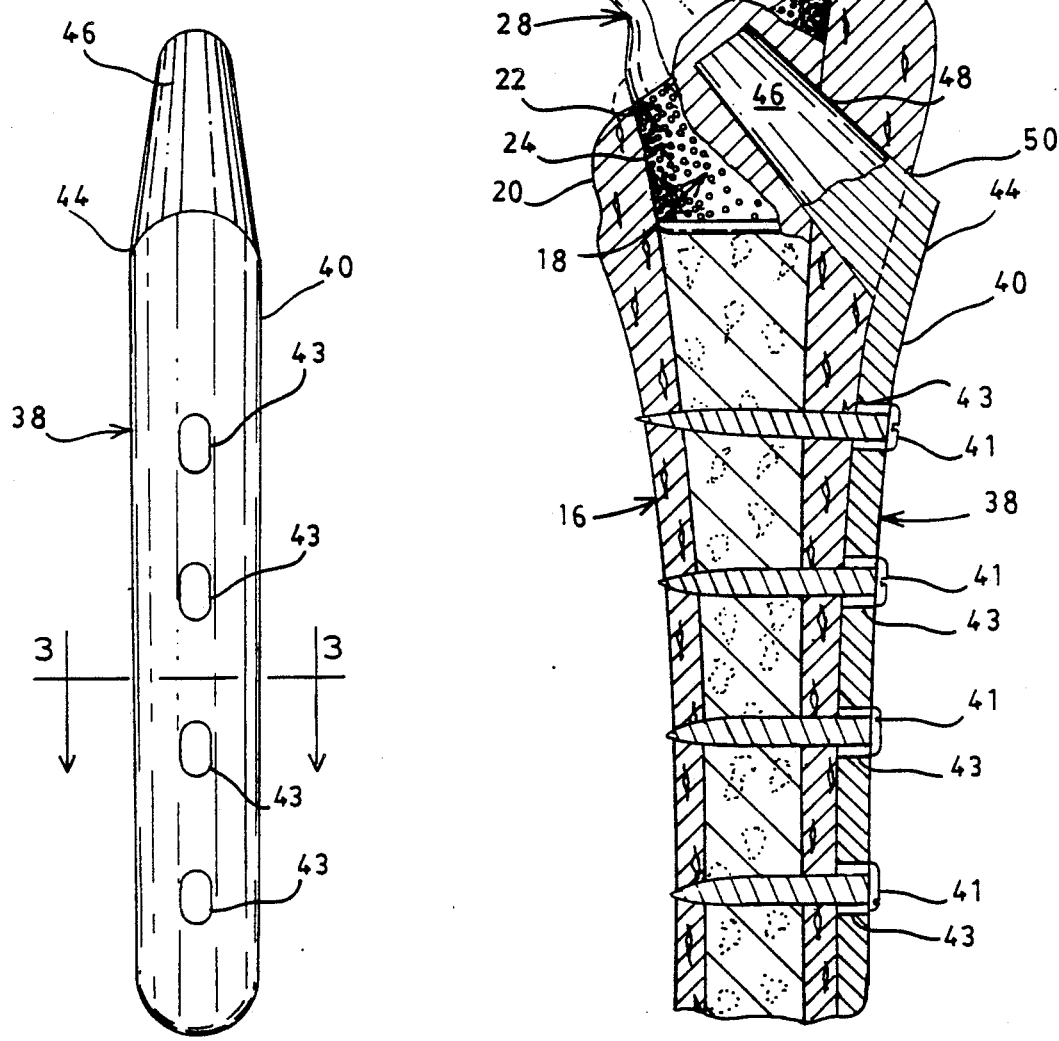
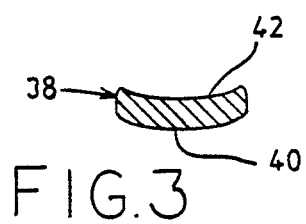

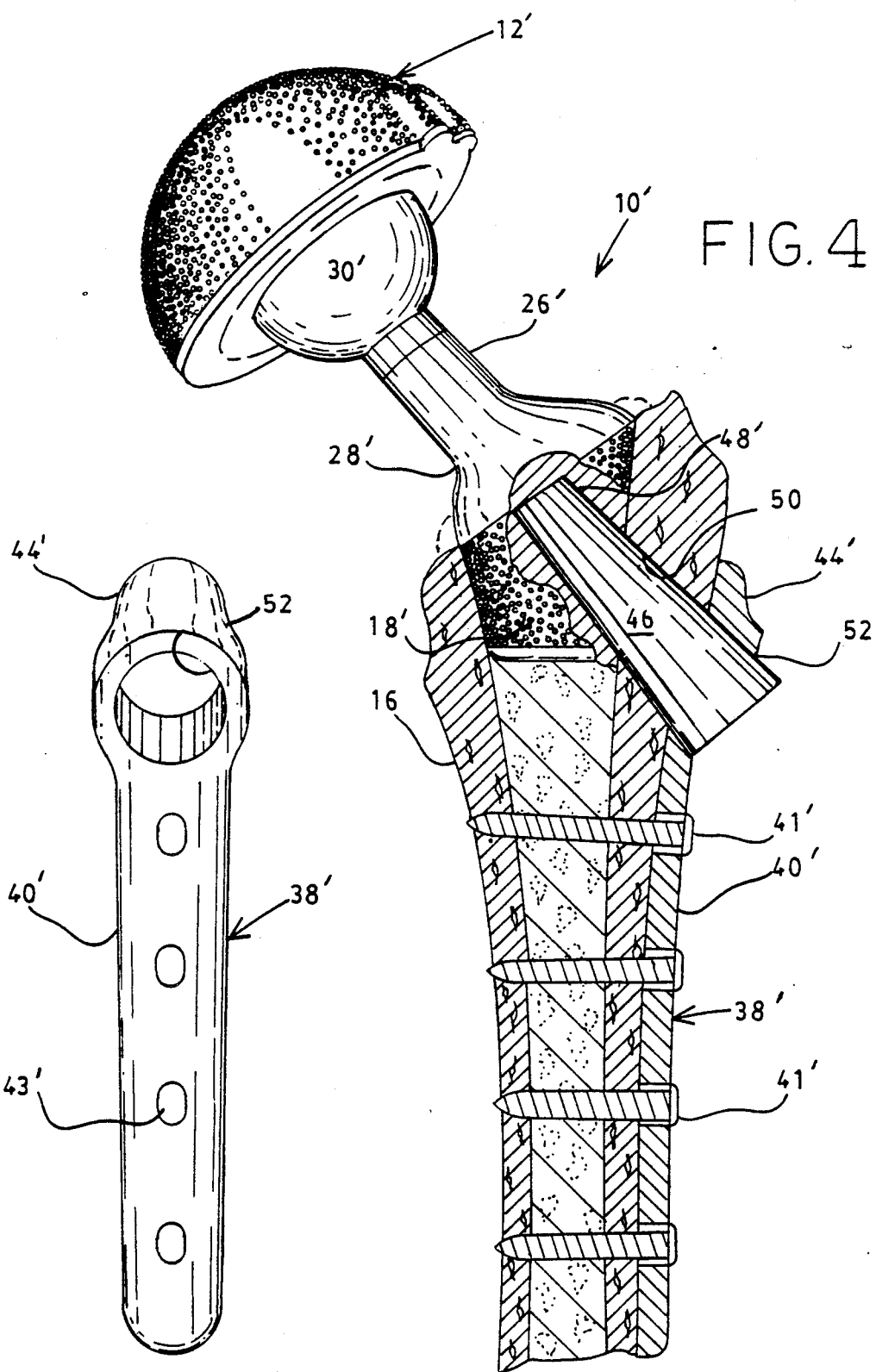

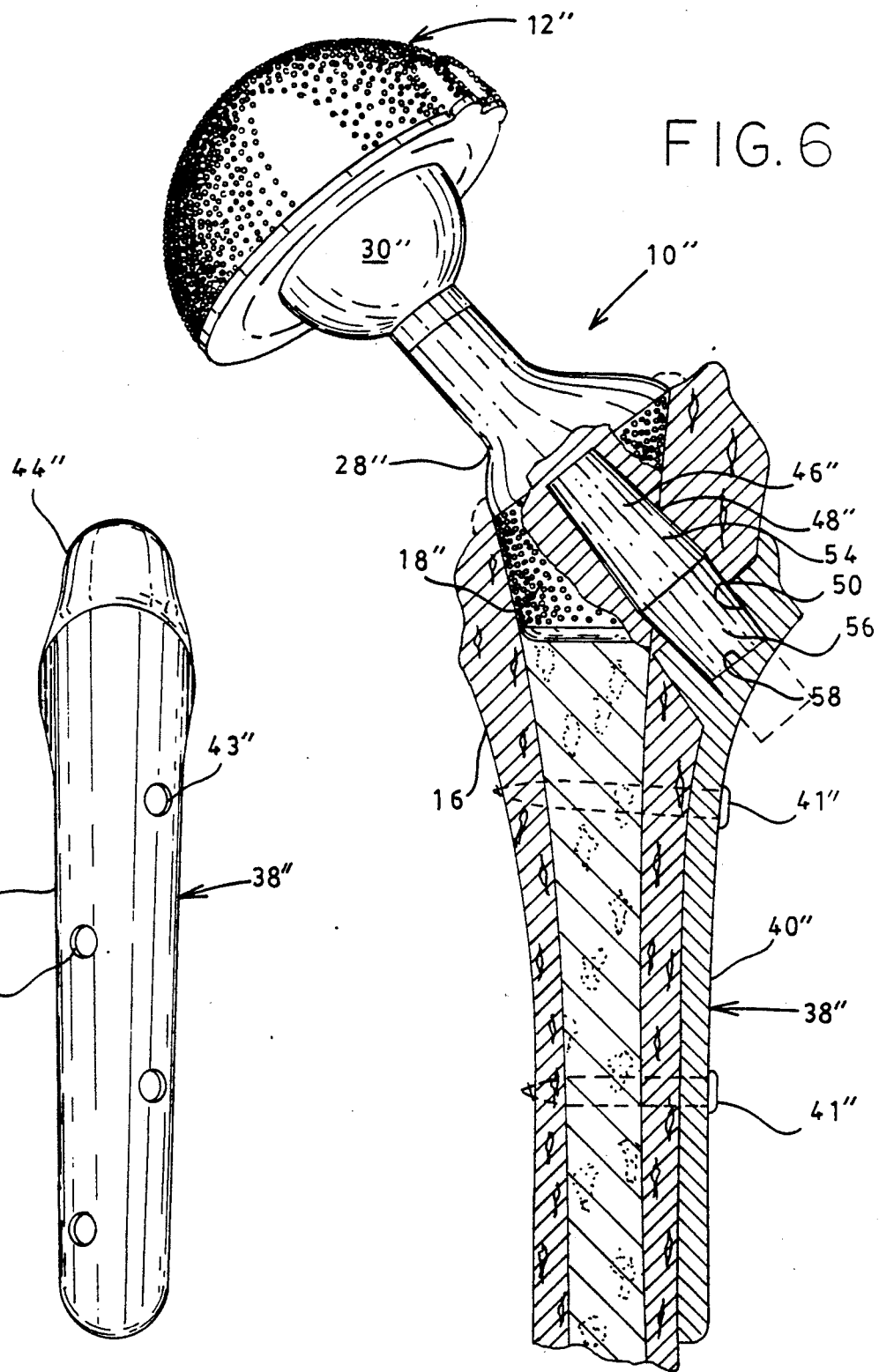

FEMORAL COMPONENT FOR A HIP PROSTHESIS

TECHNICAL FIELD

This invention relates to an improved femoral component for a hip prosthesis. In this particular invention the femoral component comprises an intramedullary proximal body carrying a neck portion and a head portion, and an extramedullary buttress plate for stabilizing the proximal body.

BACKGROUND ART

Hip prostheses for replacement of damaged or diseased human hips have long been known in the art. Heretofore, such prosthetic devices have typically included an acetabular component providing an artificial acetabulum, and a femoral component including a femoral stem for implanting in the femur and a neck portion carrying a head for being rotatably received in the artificial acetabulum. Examples of such devices are disclosed in U.S. Pat. Nos. 3,906,550; 4,365,358; 4,514,865; 4,676,797; and 4,714,471, and in European Patent No. 0000549. Generally, the femoral stem of such devices comprises a proximal portion for implantation in the proximal femur and a distal portion which is closely received in the medullary canal so as to extend into the diaphysis or shaft of the femur. The distal portion of the stem serves primarily to stabilize the proximal portion of the stem such that overall stability of the component may ensue. However, the implantation of the distal stem into the medullary canal can result in post operative pain due to stress risers that may occur at the prosthesis-bone interface. Further, the infinite variety of shapes, sizes and contours of the femur preclude precise press-fit relationships between prosthesis and bone when intramedullary stems are used. Also, the reaming of the femur necessary for the implantation of the distal stem can undermine the strength of the femur, and later removal of the distal stem should the prosthesis require replacement can be difficult and damaging to the surrounding bone structures. Moreover, the intramedullary dimensions of the femur tend to expand with aging, potentially producing loosening and pain at the distal stem region.

Therefore, it is an object of the present invention to provide a femoral component for a hip prosthesis which does not require the implantation of a distal stem in the medullary canal.

It is another object of the present invention to provide a femoral component for a hip prosthesis which is easily implanted and secured in the desired position.

Yet another object of the present invention is to provide a femoral component for a hip prosthesis which minimizes post operative pain.

Still another object of the present invention is to provide a femoral component for a hip prosthesis which minimizes structural damage to the femur upon implantation and upon later revision of the prosthesis should that become necessary.

DISCLOSURE OF THE INVENTION

Other objects and advantages will be accomplished by the present invention which provides a femoral component for a hip prosthesis. The femoral component comprises a proximal body having a lower portion for implantation into the proximal femur, and a neck portion carried by the upper portion of the proximal body. A head portion for being rotatably received in the acetabulum of an operatively associated acetabular component is mounted on the neck portion. Further, an extramedullary buttressing means is provided for supporting the proximal body in the desired implanted position. The buttressing means includes an elongated body for being secured to the exterior of the femur along a selected portion of the length of the femoral shaft, the elongated body having a proximal end portion provided with means for engaging the proximal body.

BRIEF DESCRIPTION OF THE DRAWINGS

The above mentioned features of the invention will be more clearly understood from the following detailed description of the invention read together with the drawings in which:

FIG. 1 illustrates a side elevation view, partially in section, of a femoral component of the present invention.

FIG. 2 illustrates a rear view of an extramedullary buttress plate of the femoral component of the present invention.

FIG. 3 illustrates a top view, in section, of an extramedullary buttress plate of the femoral component of the present invention.

FIG. 4 illustrates a side elevation view, partially in section, of an alternate embodiment of a femoral component of the present invention.

FIG. 5 illustrates a rear view of an alternate embodiment of an extramedullary buttress plate of the femoral component of the present invention.

FIG. 6 illustrates a side elevation view, partially in section, of a further alternate embodiment of a femoral component of the present invention.

FIG. 7 illustrates a rear view of the further alternate embodiment of an extramedullary buttress plate of the femoral component of the present invention.

BEST MODE FOR CARRYING OUT THE INVENTION

A femoral component incorporating various features of the present invention is illustrated generally at 10 in FIG. 1. The femoral component 10 is used in conjunction with an acetabular component 12 to provide a total hip prosthesis for replacing a damaged or diseased human hip. More specifically, the acetabular component 12 is implanted in the innominate bone (not shown) and defines an artificial acetabulum of the hip. Cooperatively, the femoral component 10 of the present invention is implanted in the femur 16 to replace the natural femoral neck and head.

As illustrated in FIGS. 1 and 2, the femoral component comprises a proximal body 18 for being implanted in the proximal femur 20. In the preferred embodiment the proximal body 18 has a peripheral surface 22 defining a contoured or textured (commonly porous) surface portion 24. It will be recognized by those skilled in the art that post-implant bone ingrowth into a porous surface portion 24 serves to help secure or fix the proximal body 18 in position in the proximal femur 20. Of course, it will be understood that although the porous surface portion 24 represents the preferred means for securing the proximal body 18 in place, other suitable securing means, such as a grouting agent can be utilized to secure the body 18 in the proximal femur 20.

The femoral component 10 also includes a neck portion 26 carried by the upper portion 28 of the proximal body 18, and a head portion 30 for being rotatably received in the acetabulum 14, said head portion being carried by the neck portion 26 by use of a taper interference fit configuration. In the preferred embodiment the head portion 30 is releasably secured on the outboard end 32 of the neck portion 26. To accomplish the releasable securing to the head portion 30 to the neck portion 26, the outboard end 32 of the neck portion 26 defines a morse cone 34 and the head portion 30 is provided with a receptor 36 defining tapered sidewalls for closely receiving the cone 34. Accordingly, the force-fit insertion of the cone 34 into the receptor 36 accomplishes the releasable securing of the head portion 30 on the neck portion 26. Of course, it will be appreciated that such releasable securing means is simply one preferred means for securing the head portion 30 on the neck portion 26 and other suitable means can be utilized.

In order to stabilize the implanted position of the proximal body 18 the femoral component 10 further includes an extramedullary buttress plate 38. The buttress plate 38 includes an elongated body 40 for engaging the exterior of the femur 16 along a selected portion of its length. Further, the body 40 is preferably provided with a concaved engaging surface 42, as illustrated in FIG. 3, such that the body 40 at least partially wraps around the exterior of the femur 16, thereby, facilitating the close engagement of the plate 38 and the femur 16. Means are also provided for securing the buttress plate 38 to the femur 16. In the preferred embodiment such means includes a plurality of fasteners, such as the illustrated screws 41, which are received through apertures 43 provided in the body 40 of the buttress plate 38 and anchored in the femur 16.

The body 40 of the buttress plate 38 also includes a proximal end portion 44 provided with means for engaging the proximal body 18. In the preferred illustrated embodiment of FIGS. 1 and 2, such means includes a further morse cone 46 which is releasably received by a further receptor 48 provided in the proximal body 18, the receptor 48 having tapered side walls for closely receiving the cone 46. More specifically, the cone 34 is received through a hole 50 drilled in the proximal femur 20, and the free end portion of the cone 46 is force-fittably received in the receptor 48. Resultantly, the buttress plate 38 serves to lock and support the proximal body 18 in its implanted position in the proximal femur 16. However, it will be recognized that other suitable means can be used for securing the proximal end portion 44 to the proximal body 18, and the morse cone 46 and receptor 48 represent only one preferred means.

It will also be noted that in the preferred embodiment the receptor 48 is substantially axially aligned with the neck portion 26 such that the load forces carried by the neck portion and proximal body 18 is efficiently shared and rotational and varus/valgus stability of the prothesis is enhanced.

Whereas in the embodiment of FIGS. 1 and 2 the further morse cone 46 is illustrated as being integral with the body 40 of the buttress plate 38, it is contemplated that the cone 46 can be releasably mounted in, or secured to, the buttress plate rather than integral therewith. In this regard, in FIGS. 4 and 5 an alternate embodiment of the femoral component of the present invention is illustrated at 10'. For convenience, features of the component 10 which are common to the component 10' are referenced with common prime numerals.

In the preferred illustrated embodiment of the femoral component 10' the proximal end portion 44' of the buttress plate 38' is provided with an opening 52 therethrough, preferably having a conical sidewall for force-fit reception of the morse cone 46'. Thus, after the proximal body 18' is implanted and the hole 50 is cut in the femur 16, the buttress plate 38' is placed in position and the morse cone 46' is inserted through the opening 52 in the buttress plate 38', and through the hole 50 in the femur, to be received in the receptor 48'. The buttress plate 38' is then secured to the femur 16 with the screws 41'.

A further alternate embodiment of the femoral component of the present invention is illustrated at 10" in FIGS. 6 and 7. For convenience, features of the components 10 and 10' which are common to the component 10" are referenced with common prime numerals. In the preferred illustrated embodiment of the femoral component 10" the component is provided with a connecting member 54 which defines the morse cone 46" for reception by the receptor 48" of the proximal body 18", as described above, and, a second, oppositely disposed morse cone 56. The morse cone 56 is releasably received by a receptor 58 provided in the body 40" of the buttress plate 38". It will be noted that the receptor 58 can define an aperture extending through the body 40" such that the morse cone 56 extends through the body 40" as illustrated by the broken lines 58 in FIG. 6.

With respect to the embodiment of FIGS. 6 and 7, it will be recognized that, depending upon the size and configuration of the proximal femur, the gap between the buttress plate 38" and the proximal body 18" will vary. By providing connecting members 54 having various lengths this variation in the gap between the body 18" and the plate 38" can be accommodated without the need to provide plates 38" which vary in size or configuration.

In light of the above it will be recognized that the present invention provides a femoral component for a hip prothesis having great advantages over the prior art. The use of the buttress plate 38 obviates the need for a distal stem implanted in the medullary canal of the femur, and the problems associated therewith, yet firmly supports the proximal body 18 in the desired implanted position. However, while a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A femoral component for a hip prosthesis, said femoral component being for implantation into a femur, said femur defining a proximal femur and a femoral shaft, said femoral component comprising:

a proximal body having a lower portion for implantation into said proximal femur, and an upper portion, said proximal body defining a receptor having a tapered sidewall;

a neck portion carried by said upper portion of said proximal body;

a head portion carried by said neck portion for being rotatably received in an acetabulum; and extramedullary buttressing means for supporting said proximal body in a desired implanted position, said buttressing means including an elongated body for being secured to the exterior of said femur along a selected portion of the length of said femoral shaft, said elongated body having a proximal end portion provided with means for engaging said proximal body, said means for engaging said proximal body including a protruding member defining a morse cone for being closely received in said receptor of said proximal body.

2. The femoral component of claim 1 wherein said proximal body defines a receptor, and wherein said means for engaging said proximal body includes a protruding member for being closely received in said receptor of said proximal body.

3. The femoral component of claim 1 wherein said protruding member defines a morse cone and said receptor defines a tapered sidewall for closely receiving said morse cone.

4. The femoral component of claim 1 wherein said morse cone is releasably secured to said proximal end portion of said elongated body.

5. The femoral component of claim 1 wherein said receptor is disposed in said lower portion of said proximal body so as to be disposed within said proximal femur when said proximal body is implanted, whereby said protruding member is received through an opening in said proximal femur and into said receptor.

6. The femoral component of claim 1 wherein said receptor is disposed in said lower portion of said proximal body so as to be disposed within said proximal femur when said proximal body is implanted, whereby said morse cone is received through an opening in said proximal femur and into said receptor.

7. The femoral component of claim 4 wherein said proximal end portion of said elongated body is provided with a opening therethrough having a tapered sidewall for force-fit reception of said morse cone, whereby said morse cone is releasably secured to said elongated body.

8. The femoral component of claim 6 wherein said proximal end portion of said elongated body is provided with an opening therethrough having a tapered sidewall for force-fit reception of said morse cone, whereby said morse cone is releasably secured to said elongated body.

9. The femoral component of claim 1 wherein said elongated body is provided with a plurality of selectively spaced opening for receiving screws, whereby said elongated body of said buttressing means is secured to said femur inserting said screws through said opening and threading said screws into said femur.

10. The femoral component of claim 6 wherein said elongated body is provided with a plurality of selectively spaced openings for receiving screws, whereby said elongated body of said buttressing means is secured to said femur inserting said screws through said openings and threading said screws into said femur.

11. The femoral component of claim 1 wherein said proximal body defines a first receptor, and said elongated member of said extramedullary buttressing means defines a further receptor, and wherein said means for engaging said proximal body includes a connecting member having a first morse cone for being closely received in said first receptor of said proximal body and a second morse cone for being closely received in said further receptor of said elongated body.

12. A femoral component for a hip prosthesis, said femoral component being for implantation into a femur, said femur defining a proximal femur and a femoral shaft, said femoral component comprising:
a proximal body having a lower portion for implantation into said proximal femur, and an upper portion, said lower portion of said proximal body being provided with a receptor;
a neck portion carried by said upper portion of said proximal body;
a head portion carried by said neck portion for being rotatably received in an acetabulum; and
an extramedullary buttressing plate for supporting said proximal body in a desired implanted position, said buttressing plate including an elongated body for being secured to the exterior of said femur along a selected portion of the length of said femoral shaft, said elongated body having an proximal end portion provided with a morse cone for being received through an opening in said proximal femur and into said receptor of said proximal body.

13. A femoral component for a hip prosthesis, said femoral component being for implantation into a femur, said femur defining a proximal femur and a femoral shaft, said femoral component comprising:
a proximal body having a lower portion for implantation into said proximal femur, and an upper portion, said lower portion of said proximal body being provided with a receptor;
a neck portion carried by said upper portion of said proximal body;
a head portion carried by said neck portion for being rotatably received in an acetabulum;
an extramedullary buttressing plate for supporting said proximal body in a desired implanted position, said buttressing plate including an elongated body for being secured to the exterior of said femur along a selected portion of the length of said femoral shaft, said elongated body having an proximal end portion provided with an opening defining a tapered sidewall; and
a morse cone for force-fit reception in said opening in said proximal end portion of said elongated body and for being received through an opening in said proximal femur and into said receptor of said proximal body, whereby said buttress plate is secured to said lower portion of said proximal body.

14. A femoral component for a hip prosthesis, said femoral component being for implantation into a femur, said femur defining a proximal femur and a femoral shaft, said femoral component comprising:
a proximal body having a lower portion for implantation into said proximal femur, and an upper portion, said lower portion of said proximal body being provided with a first receptor;
a neck portion carried by said upper portion of said proximal body;
a head portion carried by said neck portion for being rotatably received in an acetabulum;
an extramedullary buttressing plate for supporting said proximal body in a desired implanted position, said buttressing plate including an elongated body for being secured to the exterior of said femur along a selected portion of the length of said femoral shaft, said elongated body having an proximal end portion provided with a second receptor defining a tapered sidewall; and
a connecting member having a first morse cone for force-fit reception in said first receptor of said proximal body and a second morse cone for force-fit reception in said second receptor of said elongated body, whereby said buttress plate is secured to said lower portion of said proximal body.

15. A femoral component for a hip prosthesis, said femoral component being for implantation into a femur, said femur defining a proximal femur and a femoral shaft, said femoral component comprising:

a proximal body having a lower portion for implantation into said proximal femur, and an upper portion, said proximal body defining a first receptor;

a neck portion carried by said upper portion of said proximal body;

a head portion carried by said neck portion for being rotatably received in an acetabulum; and extramedullary buttressing means for supporting said proximal body in a desired implanted position, said buttressing means including an elongated body for being secured to the exterior of said femur along a selected portion of the length of said femoral shaft, said elongated body having a proximal end portion provided with a further receptor and means for engaging said proximal body, said means for engaging said proximal body including a connecting member having a first morse cone for being closely received in said first receptor of said proximal body and a second morse cone for being closely received in said further receptor of said elongated body.

16. A femoral component for a hip prosthesis, said femoral component being for implantation into a femur, said femur defining a proximal femur and a femoral shaft, said femoral component comprising:

a proximal body having a lower portion for intermedullary implantation into said proximal femur and an upper portion, said lower portion defining a bonding surface configured to substantially conform to the inner cortical contour of the proximal femur whereby said lower portion of said proximal body is surrounded by the cortical tissue of said proximal femur upon intermedullary implantation;

a neck portion carried by said upper portion of said proximal body;

a head portion carried by said neck portion for being rotatably received in an acetabulum; and extramedullary buttressing means for supporting said proximal body in a desired implanted position, said buttressing means including an elongated body for being secured to the exterior of said femur along a selected portion of the length of said femoral shaft, said elongated body having a proximal end portion provided with means for engaging said proximal body.

17. A femoral component for a hip prosthesis, said femoral component being for implantation into a femur, said femur defining a proximal femur and a femoral shaft, said femoral component comprising:

a proximal body having a lower portion for intermedullary implantation into said proximal femur and an upper portion, said lower portion defining a bonding surface configured to substantially conform to the inner cortical contour of the proximal femur whereby said lower portion of said proximal body is closely received by the cortical tissue of said proximal femur upon intermedullary implantation, said proximal body further defining a receptor;

a neck portion carried by said upper portion of said proximal body;

a head portion carried by said neck portion for being rotatably received in an acetabulum; and extramedullary buttressing means for supporting said proximal body in a desired implanted position, said buttressing means including an elongated body for being secured to the exterior of said femur so as to extend along a selected portion of the length of said femoral shaft, said elongated body having a proximal end portion provided with means for engaging said proximal body, said means for engaging said proximal body including a protruding member for press-fit reception in said receptor of said proximal body.

18. The femoral component of claim 17 wherein said neck portion and said receptor of said proximal body are aligned on a common axis.

* * * * *